United States Patent
Lee et al.

(10) Patent No.: US 11,872,228 B2
(45) Date of Patent: Jan. 16, 2024

(54) PHARMACEUTICAL COMPOSITION CONTAINING THIAMINE DERIVATIVE FOR PREVENTION OR TREATMENT OF SEPSIS

(71) Applicants: KYUNGPOOK NATIONAL UNIVERSITY INDUSTRY-ACADEMIC COOPERATION FOUNDATION, Daegu (KR); KYUNGPOOK NATIONAL UNIVERSITY HOSPITAL, Daegu (KR)

(72) Inventors: In Kyu Lee, Daegu (KR); Eun Jung Choi, Daegu (KR); Chang Hyun Jeon, Daegu (KR); Tae-Hwan Kwon, Daegu (KR); Dong Ho Park, Daegu (KR)

(73) Assignees: KYUNGPOOK NATIONAL UNIVERSITY INDUSTRY-ACADEMIC COOPERATION FOUNDATION, Daegu (KR); KYUNGPOOK NATIONAL UNIVERSITY HOSPITAL, Daegu (KR)

( * ) Notice: Subject to any disclaimer, the term of this patent is extended or adjusted under 35 U.S.C. 154(b) by 24 days.

(21) Appl. No.: 17/557,358

(22) Filed: Dec. 21, 2021

(65) Prior Publication Data

US 2022/0347178 A1 Nov. 3, 2022

(30) Foreign Application Priority Data

Apr. 22, 2021 (KR) .......................... 10-2021-0052256

(51) Int. Cl.
| | | |
|---|---|---|
| *C07D 239/24* | (2006.01) | |
| *C07D 405/12* | (2006.01) | |
| *A61K 31/505* | (2006.01) | |
| *A61K 31/506* | (2006.01) | |
| *A61P 31/00* | (2006.01) | |
| *A61K 31/51* | (2006.01) | |

(52) U.S. Cl.
CPC .................................. *A61K 31/51* (2013.01)

(58) Field of Classification Search
CPC .. C07D 239/24; C07D 405/12; A61K 31/506; A61K 31/505; A61P 31/00
See application file for complete search history.

(56) References Cited

PUBLICATIONS

Do et al., Fursultiamine Alleviates Choroidal Neovascularization by Suppressing Inflammation and Metabolite Reprogramming, Investigative Ophthalmology & Visual Science, vol. 61, No. 12, Article 24, pp. 1-9 (Year: 2020).*
Choi et al., "Allithiamine Exerts Therapeutic Effects on Sepsis by Modulating Metabolic Flux during Dendritic Cell Activation," Molecules and Cells 43(11):964-973 (2020).
Kyungpook National University Hospital, KR clinical trial database search result, Alcotamin, "Effect of fursultiamine as adjuvant for treatment of sepsis" approved and published Dec. 16, 2020, retrieved on Jan. 22, 2021 (1 page).

* cited by examiner

*Primary Examiner* — Brenda L Coleman
(74) *Attorney, Agent, or Firm* — Clark & Elbing LLP; Susan M. Michaud

(57) ABSTRACT

The present disclosure is a pharmaceutical composition for the prevention or treatment of sepsis containing a thiamine derivative or a pharmaceutically acceptable salt thereof, wherein the pharmaceutical composition of the present disclosure can be used for the prevention, alleviation, or treatment of sepsis by containing fursultiamine or allithiamine to inhibit the expressions of CD40, CD86, and TNFα.

5 Claims, 8 Drawing Sheets

PHARMACEUTICAL COMPOSITION CONTAINING THIAMINE DERIVATIVE FOR PREVENTION OR TREATMENT OF SEPSIS

BACKGROUND OF THE INVENTION

Field of the Invention

The present disclosure was made with the support of the Ministry of Science and ICT, Republic of Korea, under project identification No. 1711111722 and project No. 2017R1A2B3006406, which was conducted in the project named "New Therapeutic Strategy for Chronic Inflammation and Metabolic Syndrome through Mitochondria-Associated ER Membrane (MAM) Interaction and Pyruvate Dehydrogenase Kinase (PDK) Activity Regulation" in the research program titled "Individual Basic Research (the Ministry of Science and ICT (R&D))" by the Kyungpook National University under management of the National Research Foundation of Korea, from 1 Mar. 2020 to 28 Feb. 2021, and the present disclosure was also made with the support of the Ministry of Health and Welfare, Republic of Korea, under project identification No. 1465030348 and project No. HI16C1501080020, which was conducted in the project named "Construction of Preclinical Core Platform for Diabetes and Metabolic Syndrome" in the research program titled "Leading Characterization Research Program (R&D)", by the Kyungpook National University Hospital, under management of the Korea Health Industry Development Institute, from 1 Jan. 2020 to 31 Dec. 2020.

This application claims priority to and the benefit of Korean Patent Application No. 10-2021-0052256 filed in the Korean Intellectual Property Office on 22 Apr. 2021, the disclosure of which is incorporated herein by reference.

The present disclosure relates to a composition containing a thiamine derivative and, more specifically, to a pharmaceutical composition for the prevention or treatment of sepsis containing allithiamine or fursultiamine in a pharmaceutically effective amount.

The present disclosure relates to a method for alleviating, preventing, or treating sepsis, the method including administering to a subject a composition containing a thiamine derivative or a pharmaceutically acceptable salt thereof.

The present disclosure relates to a method for inhibiting the expression of a cell surface marker, a TNF superfamily, or a cytokine, the method including administering to a subject a composition containing a thiamine derivative or a pharmaceutically acceptable salt thereof.

Description of the Prior Art

Sepsis is a condition in which a severe inflammatory response occurs all over the body by a microbial infection. Sepsis is caused by microbial infections. Sepsis-causing pathogens are streptococci, staphylococci, *Escherichia coli*, pneumococcus, *Pseudomonas aeruginosa*, fungi, *Klebsiella* mutants, and the like.

Any organ of the body may be a site of causative infection, and pneumonia, pyelonephritis, meningitis, cellulitis, infectious endocarditis, peritonitis, bedsores, cholecystitis, cholangitis, and the like may be causes of sepsis. The occurrence of such infections may cause sepsis by the invasion of causative microorganisms thereof into the blood. Even in the absence of invasion of microorganisms into the blood, systemic sepsis may be caused by an inflammatory response in a part of the body and the production of inflammatory substances.

Examples of early symptoms of sepsis may include a rapid breathing rate or neurological disorders, such as loss of orientation (awareness of time, place, and person) or delirium. The skin may appear blue due to the decrease in blood pressure and the reduction in amount of blood supplied to the terminal parts of the body. In the presence of bacteremia (having bacteria circulating in the blood), bacteria may travel along bloodstream, and settle in particular areas of the body to cause pathological changes in those areas. Nausea, vomiting, diarrhea, and intestinal paralysis may occur as gastrointestinal symptoms, and a digestive bleeding symptom may be seen in severe stressful situations.

Sepsis usually has a death risk of 20 to 35%, but septic shock caused by rapid worsening of sepsis is a very fatal disease with 40 to 60% mortality. Therefore, a body infection site causing sepsis is promptly found through the physical examination, blood test, and imaging test, and the infection is then treated with an appropriate antibiotic. In order to find a causative pathogen of sepsis, an examination in which the patient's blood is collected to cure bacteria is required, but this takes about 3 to 5 days. Thus, if the patient is in a critical condition, an empirical therapy needs to be performed before culturing examination results.

However, sepsis is a disease for which fundamental treatments have not yet been developed, and the global market for sepsis treatments is estimated to be USD 7.4 billion (KRW about 8.3 trillion, as of 2017).

SUMMARY OF THE INVENTION

The present inventors identified that the administration of fursultiamine or allithiamine to a lipopolysaccharide (LPS)-induced sepsis mouse model produced effects of increasing the survival rate of mice and inhibiting the expressions of inflammatory cytokines, such as CD40, CD86, IL-1$\beta$, and TNF$\alpha$.

Accordingly, an aspect of the present disclosure is to provide a pharmaceutical composition for the prevention or treatment of sepsis containing a thiamine derivative or a pharmaceutically acceptable salt thereof.

Another aspect of the present disclosure is to provide a food composition for the alleviation of sepsis containing a thiamine derivative or a pharmaceutically acceptable salt thereof.

Still another aspect of the present disclosure is to provide a pharmaceutical composition for the inhibition of the expression of a cell surface marker, the pharmaceutical composition containing a thiamine derivative or a pharmaceutically acceptable salt thereof.

Still another aspect of the present disclosure is to provide a pharmaceutical composition for the inhibition of the expression of a TNF superfamily, the pharmaceutical composition containing a thiamine derivative or a pharmaceutically acceptable salt thereof.

Still another aspect of the present disclosure is to provide a pharmaceutical composition for the inhibition of the expression of a cytokine, the pharmaceutical composition containing a thiamine derivative or a pharmaceutically acceptable salt thereof.

Still another aspect of the present disclosure is to provide a method for alleviating, preventing, or treating sepsis, the method including administering to a subject a composition containing a thiamine derivative or a pharmaceutically acceptable salt thereof.

Still another aspect of the present disclosure is to provide a method for inhibiting the expression of a cell surface marker, a TNF superfamily, or a cytokine, the method including administering to a subject a composition containing a thiamine derivative or a pharmaceutically acceptable salt thereof.

The present disclosure is directed to a pharmaceutical composition for the prevention or treatment of sepsis, the pharmaceutical composition containing a thiamine derivative as an active ingredient, and the pharmaceutical composition of the present disclosure can be used for the prevention, alleviation, or treatment of sepsis by containing fursultiamine or allithiamine.

The present disclosure is directed to a method for alleviating, preventing, or treating sepsis, the method including administering to a subject a composition containing a thiamine derivative or a pharmaceutically acceptable salt thereof, and the use of the method of the present disclosure can alleviate, prevent, or treat sepsis.

The present disclosure is directed to a method for inhibiting the expression of a cell surface marker, a TNF superfamily, or a cytokine, the method including administering to a subject a composition containing a thiamine derivative or a pharmaceutically acceptable salt thereof, and the use of the method of the present disclosure can inhibit the expression of a cell surface marker, a TNF superfamily, or a cytokine.

Hereinafter, the present disclosure will be described in more detail.

In an accordance with an aspect of the present disclosure, there is provided a pharmaceutical composition for the prevention or treatment of sepsis containing a thiamine derivative represented by chemical formula 1 below or a pharmaceutically acceptable salt thereof:

[Chemical Formula 1]

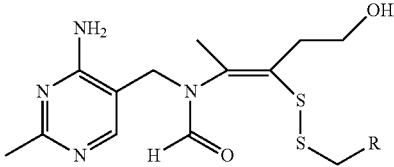

wherein R is any one selected from the group consisting of

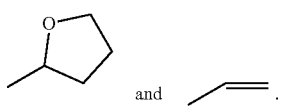

In the present disclosure, the thiamine derivative may be at least one type selected from the group consisting of fursultiamine, allithiamine, and benfotiamine. For example, the thiamine derivative may be fursultiamine and allithiamine, but is not limited thereto.

In the present disclosure, the pharmaceutical composition may be used for the prevention and/or treatment of sepsis, but is not limited thereto.

Sepsis may refer to a condition in which an inflammation response, such as a fever, a rapid pulse, an increased breathing rate, or an elevated or reduced leukocyte count, occurs all over the body due to microbial infections or the like. Sepsis may accompany a shock or disability when not treated appropriately at the right time, and may result in a death in a severe case.

In the present disclosure, the pharmaceutical composition may contain a thiamine derivative in a pharmaceutically effective amount.

As used herein, the term "pharmaceutically effective amount" refers to an amount that is sufficient to attain efficacy or activity of the aforementioned thiamine derivatives.

In the present disclosure, the pharmaceutical composition may contain a pharmaceutically acceptable carrier, but is not limited thereto.

In the present disclosure, the pharmaceutically acceptable carrier contained in the pharmaceutical composition is one that is typically used for formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oils, and the like.

In the present disclosure, the pharmaceutical composition may further contain, but is not limited to, a lubricant, a wetting agent, a sweetening agent, a flavoring agent, an emulsifier, a suspending agent, a preservative, and the like, in addition to the above ingredients.

The pharmaceutical composition according to the present disclosure may be administered to mammals including humans through various routes. The manner of administration may be any manner that is typically employed, and the administration may be conducted in any manner employing an oral, dermal, intravenous, intramuscular, or subcutaneous route, and for example, the administration may be conducted in a manner employing an intravenous route, but is not limited thereto.

The concentration of fursultiamine contained in the pharmaceutical composition of the present disclosure may be 0.01 to 200 µM, µM, 0.01 to 150 µM, 0.01 to 100 µM, 0.01 to 50 µM, 0.01 to 10 µM, 0.1 to 200 µM, 0.1 to 150 µM, 0.1 to 100 µM, 0.1 to 50 µM, 0.1 to 10 µM, 1 to 200 µM, 1 to 150 µM, 1 to 100 µM, 1 to 50 µM, or 1 to 10 µM, and for example, may be 1 to 10 µM, but is not limited thereto.

The concentration of allithiamine contained in the pharmaceutical composition of the present disclosure may be 0.001 to 20 µM, 0.001 to 15 µM, 0.001 to 10 µM, 0.001 to 5 µM, 0.001 to 1 µM, 0.01 to 20 µM, 0.01 to 15 µM, 0.01 to 10 µM, 0.01 to 5 µM, 0.01 to 1 µM, 0.1 to 200 µM, 0.1 to 15 µM, 0.1 to 10 µM, 0.1 to 5 µM, or 0.1 to 1 µM, and for example, may be 0.1 to 1 µM, but is not limited thereto.

The pharmaceutical composition of the present disclosure may be prepared into a unit dosage form or a multi-dose container along with a pharmaceutically acceptable carrier and/or excipient according to a method that can be easily performed by a person having ordinary skills in the art to which the present disclosure pertains.

The formulation of the pharmaceutical composition of the present disclosure may be in the form of a solution in an oily or aqueous medium, a suspension, an emulsion, an extract, a powder, granules, a tablet, a capsule, or a gel (e.g., a hydrogel), but is not limited thereto.

The pharmaceutical composition of the present disclosure may further contain a dispersant or a stabilizer, but is not limited thereto.

In the present disclosure, sepsis may be a condition in which a severe inflammatory response occurs all over the body by a microbial infection, and the cause of sepsis is an infection by microorganisms.

A causative pathogen of the sepsis may be at least one species selected from the group consisting of streptococci, staphylococci, *Escherichia coli*, pneumococcus, *Pseudomonas aeruginosa*, fungi, *Klebsiella* mutants, but is not limited thereto.

As used herein, the term "prevention" may refer to any action that suppresses sepsis or delays the progression thereof by administration of the pharmaceutical composition according to the present disclosure.

As used herein, the term "treatment" may refer to any action that alleviates or advantageously changes symptoms of sepsis by administration of the pharmaceutical composition according to the present disclosure.

In accordance with another aspect of the present disclosure, there is provided a food composition for the alleviation of sepsis containing a thiamine derivative represented by chemical formula 1 below or a pharmaceutically acceptable salt thereof:

[Chemical Formula 1]

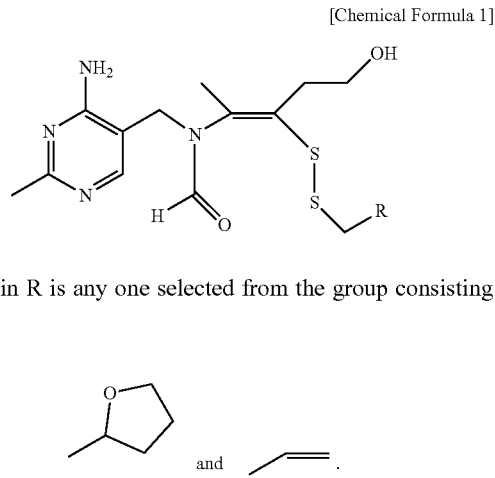

wherein R is any one selected from the group consisting of

In the present disclosure, the food composition may be a food additive. The food composition may be added as it is or may be used along with other food or food ingredients, and may be appropriately used by a conventional method.

In the present disclosure, examples of the food may include meat, sausage, bread, chocolate, candies, snacks, confectionery, pizza, ramen, other noodles, gums, dairy products including ice creams, various kinds of soups, beverages, teas, drinks, alcoholic beverages, vitamin complexes, and the like, but are not particularly limited thereto, and may encompass all foods in the accepted meaning.

The beverages may contain as additive ingredients various kinds of flavoring agents or natural carbohydrates. The aforementioned natural carbohydrates may include monosaccharides, such as glucose and fructose, disaccharides, such as maltose and sucrose, natural sweeteners, such as dextrin and cyclodextrin, and synthetic sweeteners, such as saccharin and aspartame. The proportion of the natural carbohydrates may be appropriately determined by the selection of a person skilled in the art.

In the present disclosure, the food composition may contain various types of nutritional supplements, vitamins, electrolytes, flavors, colorants, pectic acid and salts thereof, alginic acid and salts thereof, organic acids, protective colloidal thickeners, pH adjusters, stabilizers, preservatives, glycerin, alcohols, carbonating agents used in carbonated drinks, and the like. Furthermore, the food composition of the present disclosure may contain fruit flesh for manufacturing natural fruit juices, fruit juice drinks, and vegetable drinks. These ingredients may be used independently or in combination. The proportions of these ingredients may also be appropriately selected by a person skilled in the art.

In accordance with still another aspect of the present disclosure, there is provided a pharmaceutical composition for the inhibition of the expression of a cell surface marker, the pharmaceutical composition containing a thiamine derivative represented by chemical formula 1 below or a pharmaceutically acceptable salt thereof:

[Chemical Formula 1]

wherein R is any one selected from the group consisting of

In the present disclosure, the cell surface marker may be at least one type selected from the group consisting of CD2, CD27, CD28, CD40, CD80, CD86, CD137, CD226, CD276, GITR, ICOS, OX-40, and CD70, and examples thereof may be CD40 and CD86, but are not limited thereto.

Especially, cluster of differentiation 40 (CD40) refers to a protein that is expressed in an antigen presenting cell (APC), wherein the protein activates the antigen presenting cell itself.

In addition, CD40 may mediate T cell-dependent immunoglobulin class switching, B cell development, and immune responses.

Meanwhile, cluster of differentiation 86 (CD86) refers to a protein that is expressed in dendritic cells, macrophages, B cells, and antigen presenting cells, wherein the protein provides costimulatory signals necessary for the activation and survival of T cells.

In addition, CD86 may be used to signal self-regulation and cell-cell association or signal attenuation of regulation and cell-cell dissociation, according to the ligand to be bound.

In accordance with still another aspect of the present disclosure, there is provided a pharmaceutical composition for the inhibition of the expression of a TNF superfamily, the pharmaceutical composition containing a thiamine derivative represented by chemical formula 1 below or a pharmaceutically acceptable salt thereof:

[Chemical Formula 1]

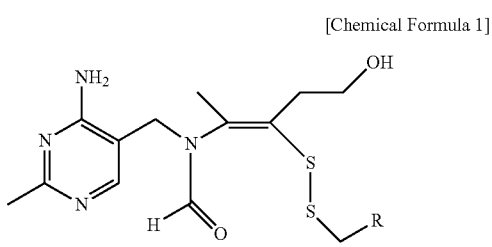

wherein R is any one selected from the group consisting of

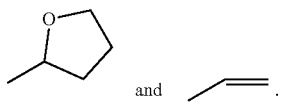

In the present disclosure, the TNF superfamily may be at least one type selected from the group consisting of TNFα, IL6, IL-1β, LTa, LTb, LIGHT, TWEAK, APRIL, BAFF, TL1A, GITRL, OX40L, CD40L (CD154), FASL, CD27L, CD30L, 4-1BBL, TRAIL, and RANK ligands, and examples thereof may be TNFα and IL-1β, but are not limited thereto.

Especially, tumor necrosis factor-a (TNFα) may be the prototypical member of the tumor necrosis factor (TNF) superfamily of proteins that share a primary function of regulating cell survival and cell death. One structural feature common to all known members of the TNF superfamily may be the formation of trimeric complexes that bind to and activate specific TNF superfamily receptors.

In addition, TNFα may refer to a protein that exists in soluble and transmembrane forms and signals through two receptors, known as TNFR1 and TNFR2, with distinct functional endpoints.

In accordance with still another aspect of the present disclosure, there is provided a pharmaceutical composition for the inhibition of the expression of a cytokine, the pharmaceutical composition containing a thiamine derivative represented by chemical formula 1 below or a pharmaceutically acceptable salt thereof:

[Chemical Formula 1]

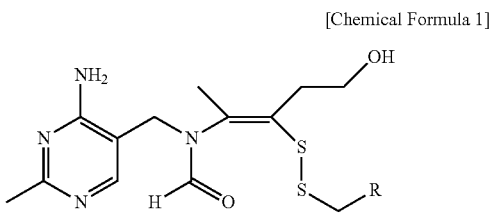

wherein R is any one selected from the group consisting of

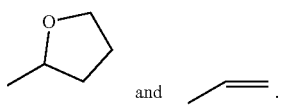

In the present disclosure, the cytokine may be at least one type selected from the group consisting of TIMP metallopeptidase inhibitor 2 (TIMP-2), transforming growth factor beta (TGF-b), regulated on activation, normal T cell expressed and secreted (RANTES), cytokine-induced neutrophil chemoattractant 3 (CINC-3), EOTAXIN, granulocyte-macrophage colony-stimulating factor (GM-CSF), interferon-gamma (IFN-gamma), IL-1β, IL-3, IL-6, IL-8, IL-10, IL-12p40, IL-13, IL-16, interferon gamma-induced protein 10 (IP-10), leptin, monocyte chemoattractant protein 2 (MCP-2), monokine induced by gamma interferon (MIG), macrophage inflammatory protein-3 alpha (MIP-3a), beta-nerve growth factor (b-NGF), soluble tumor necrosis factor receptor I (sTNFRI), and platelet-derived growth factor-bb (PFGF-bb), and an example thereof may be IL-1β, but is not limited thereto.

In accordance with still another aspect of the present disclosure, there is provided a method for alleviating, preventing, or treating sepsis, the method including: administering to a subject a composition containing a thiamine derivative represented by chemical formula 1 or a pharmaceutically acceptable salt thereof:

[Chemical Formula 1]

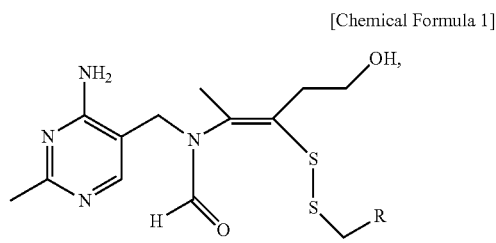

wherein R is any one selected from the group consisting of

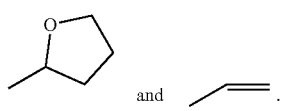

In accordance with still another aspect of the present disclosure, there is provided a method for inhibiting the expression of a cell surface marker, a TNF superfamily, or a cytokine, the method including:

administering to a subject a composition containing a thiamine derivative represented by chemical formula 1 or a pharmaceutically acceptable salt thereof:

[Chemical Formula 1]

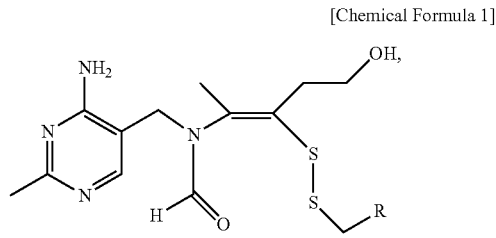

wherein R is any one selected from the group consisting of

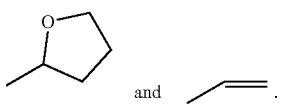
and /=.

The present disclosure is directed to a pharmaceutical composition for the prevention or treatment of sepsis, the pharmaceutical composition containing a thiamine derivative or a pharmaceutically acceptable salt thereof, and the administration of fursultiamine or allithiamine to a sepsis-induced mouse model produced excellent effects of increasing the survival rate of a mouse model and inhibiting the expressions of IL-1β, TNFα, CD40, and CD86.

DETAILED DESCRIPTION OF THE EXEMPLARY EMBODIMENTS

Hereinafter, the present disclosure will be described in more detail with reference to exemplary embodiments. These exemplary embodiments are provided only for the purpose of illustrating the present disclosure in more detail, and therefore, according to the purpose of the present disclosure, it would be apparent to a person skilled in the art that these examples are not construed to limit the scope of the present disclosure.

Experimental Example 1: Measurement of Humane Endpoint of LPS-Induced Murine Sepsis Model A dose of 50 mg/kg of lipopolysaccharide (LPS) corresponds to the "lethal dose for 50 percent kill" that kills half of the population within 24 hours. Mice were subjected to intraperitoneal injection of 50 mg/kg LPS in 1×PBS for a vehicle control, and when the mice showed the signs of the moribund state, such as impaired motility, labored breathing, or inability to maintain an upright position, the mice were sacrificed by $CO_2$ euthanasia, and the point was recorded as a humane endpoint. (The signs of the moribund state: impaired mobility, inability to maintain upright position, prolonged lack of activity and labored breathing)

All animal studies were performed according to protocols approved by Kyungpook National University (permit No. 2019-0003) and under recommendations for the proper use and care of the specific pathogen-free housing facility at Kyungpook University.

Figure 1:
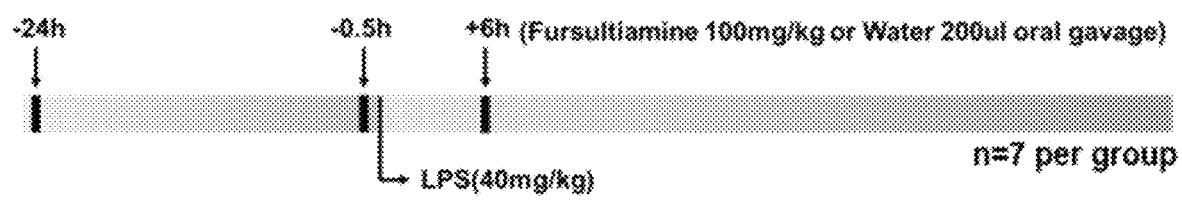
FIG. 1 shows a schematic diagram of the whole experimental schedule according to the present disclosure.
Figure 2:
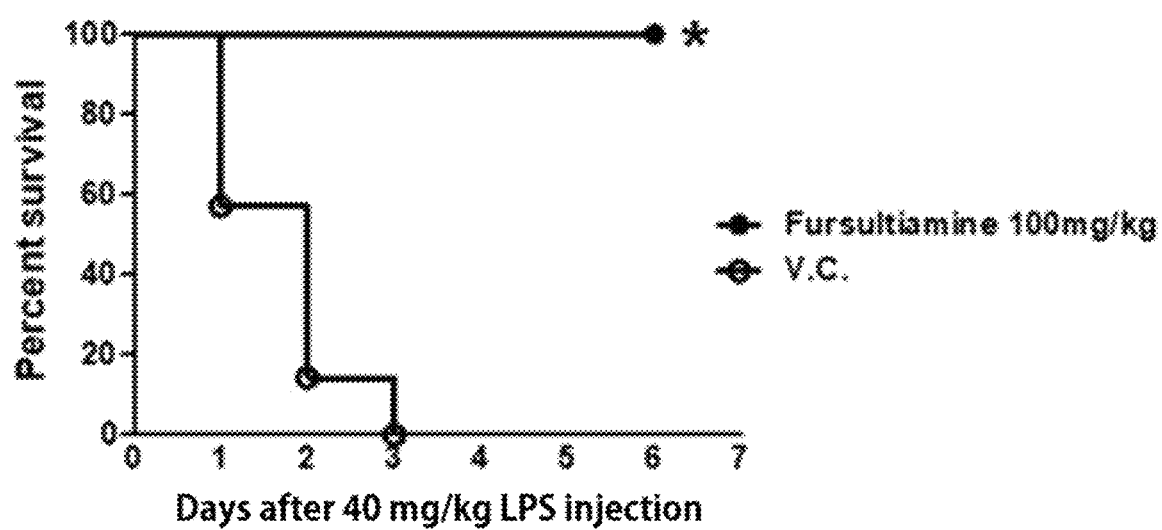
FIG. 2 shows a graph showing the survival rate over time after LPS injection in control mice intraperitoneally injected with lipopolysaccharide (LPS) and test group mice administered LPS along with fursultiamine.

Experimental Example 2: Measurement of Survival Rate of Murine Sepsis Model 2-1. Fursultiamine Treatment on Murine Sepsis Model Six- to eight-week old C57BL/6J male mice were grouped, each group containing seven mice. The whole experimental schedule is shown FIG. 1. The mice were fed fursultiamine 24 hours and 30 minutes before intraperitoneal injection of 40 mg/kg LPS, and then again administered fursultiamine 6 hours after the intraperitoneal injection, and then the survival rates of the mice were monitored and the results are shown in FIG. 2 and Table 1.

TABLE 1

| Days | Percent survival (%) | | | | | | | |
|---|---|---|---|---|---|---|---|---|
| | 0 d | 1 d | 2 d | 3 d | 4 d | 5 d | 6 d | 7 d |
| Fursultiamine 100 mg/kg | 100 | 100 | 100 | 100 | 100 | 100 | 100 | 100 |
| V.C | 100 | 57.1% | 14.2% | 0 | 0 | 0 | 0 | 0 |

(V.C. designating control mice not fed fursultiamine)

As can be identified in FIG. 2 and Table 1, the mice fed 100 mg/kg fursultiamine were not dead despite intraperitoneal injection of 40 mg/kg LPS, whereas the mice not fed fursultiamine were all dead three days after LPS injection.

2-2. Allithiamine Treatment on Murine Sepsis Model

Six- to eight-week old C57BL/6J male mice were grouped, each group containing six mice. The mice were intravenously (I.V.) administered 5 mg/kg allithiamine immediately before intraperitoneal injection of 50 mg/kg LPS, and then the survival rates were monitored (allithiamine 5 mg/kg co-treatment). In addition, the mice were intravenously administered 5 mg/kg allithiamine three hours after LPS injection, and then the survival rates were monitored (allithiamine 5 mg/kg 3 h-delayed co-treatment), and the results are shown in FIG. 3 and Table 2.

TABLE 2

| Hours | Percent survival (%) | | | | | | | | | | | |
|---|---|---|---|---|---|---|---|---|---|---|---|---|
| | 0 h | 20 h | 24 h | 28 h | 32 h | 36 h | 40 h | 44 h | 48 h | 52 h | 56 h | 60 h |
| Allithiamine 5 mg/kg co-treatment | 100 | 100 | 83.3 | 83.3 | 83.3 | 66.7 | 66.7 | 66.7 | 66.7 | 66.7 | 66.7 | 66.7 |
| Allithiamine 5 mg/kg 3 h-delayed treatment | 100 | 100 | 100 | 83.3 | 83.3 | 83.3 | 83.3 | 66.7 | 66.7 | 66.7 | 66.7 | 66.7 |
| V.C | 100 | 100 | 83.3 | 33.3 | 16.7 | 0 | 0 | 0 | 0 | 0 | 0 | 0 |

Figure 3:
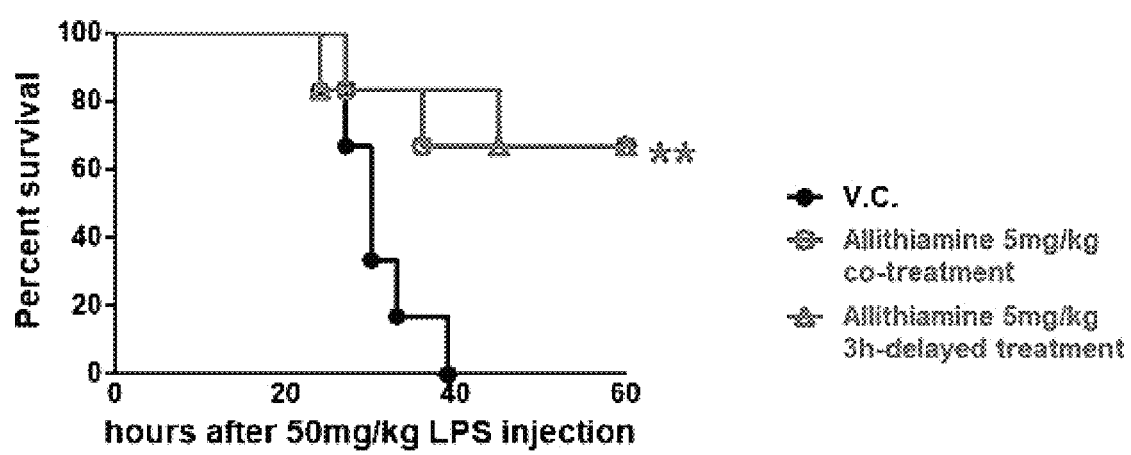
FIG. 3 shows a graph showing the survival rate over time in control mice intraperitoneally injected with LPS, test group mice administered LPS along with allithiamine, and test group mice administered allithiamine 3 hours after LPS injection.

As can be identified in FIG. 3 and Table 2, when the mice were administered allithiamine before LPS injection, 66.7% of the mice were live even 60 hours after LPS injection, whereas all the mice of the control (V.C.) injected with LPS alone were dead. Considering that 66.7% of the mice were live even 60 hours after LPS injection even when administered allithiamine 3 hours after LPS injection, even the administration of allithiamine after LPS injection were identified to improve the survival rates.

Experimental Example 3: TNFα, CD40, and CD86 Expression Inhibition by Thiamine Derivatives 3-1. Inhibition of TNFα Expression Bone marrow was extracted from the legs of six- to eight-week old C57BL/6J male mice, and subjected to red blood cell (RBC) lysis, followed by differentiation into dendritic cells in RPMI 1640 medium (10% fetal bovine serum (FBS) and 1% penicillin-streptomycin) along with 20 ng/ml granulocyte-macrophage colony-stimulating factor (GM-CSF) for six days. The dendritic cells at $1\times10^6$ cells/mL were treated with benfotiamine and fursultiamine at different concentrations of 0, 1, 10, and 100 and allithiamine at different concentrations of 0, 1, and 10 μM.

Figure 4:
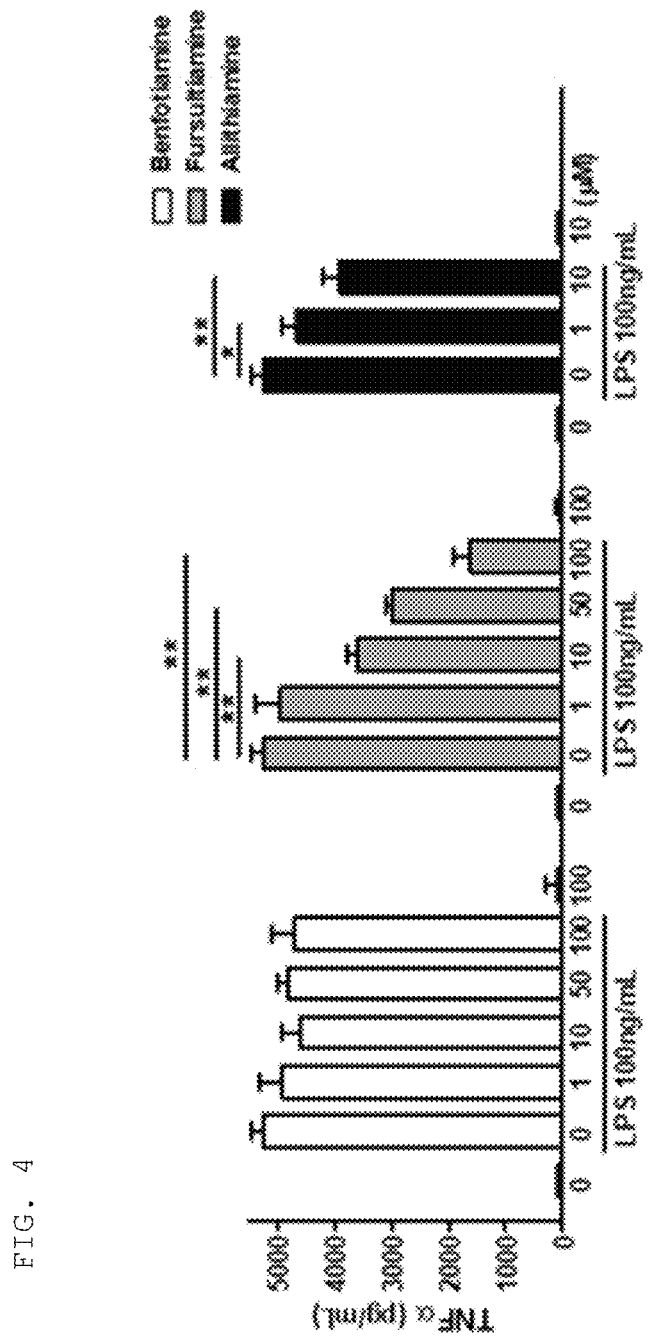
FIG. 4 shows graphs comparing CD40 expression levels in mice administered different concentrations of thiamine derivatives along with LPS.

Thereafter, the dendritic cells were activated with 100 ng/mL LPS for 18 hours. TNFα was assessed in supernatants using the enzyme-linked immunospecific assay (ELISA), and the results are shown in FIG. 4 and Table 3.

TABLE 3

| | TNFα (pg/mL) | | | | | | |
|---|---|---|---|---|---|---|---|
| Benfotiamine | 0 μM* | 0 μM | 1 μM | 10 μM | 50 μM | 100 μM | 100 μM* |
| | 93.68 | 5,248.97 | 4,909.05 | 4,614.42 | 4,806.97 | 4,696.43 | 84.82 |
| Fursultiamine | 0 μM* | 0 μM | 1 μM | 10 μM | 50 μM | 100 μM | 100 μM* |
| | 93.68 | 5,248.97 | 4,954.64 | 3,600.63 | 3,003.47 | 1,628.26 | 38.37 |
| Allithiamine | 0 μM* | 0 μM | 1 μM | 10 μM | 10 μM* | — | — |
| | 93.68 | 5,248.97 | 4,654.84 | 3,919.75 | 78.51 | — | — |

(*Dendritic cells are not stimulated by 100 ng/mL LPS)

As can be seen from FIG. 4 and Table 3, benfotiamine could not inhibit the TNFα expression increased by LPS, whereas fursultiamine significantly inhibited the TNFα expression to levels of about 68.60%, about 57.22%, and about 31.02% at the concentrations of 10 μM, 50, and 100 μM, respectively, and allithiamine significantly inhibited the TNFα expression to levels of about 88.68% and about 74.68% at the concentrations of 1 μM, and 10 μM, respectively.

3-2. Inhibition of IL-1β Expression

Figure 5:
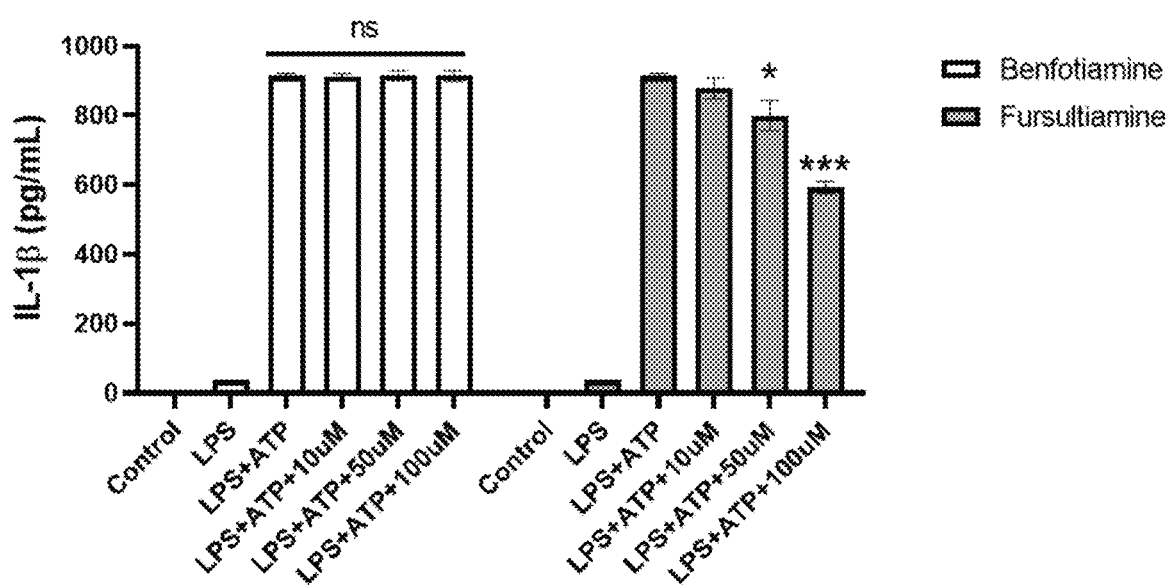
FIG. 5 shows graphs comparing IL-1β expression levels in mice administered different concentrations of thiamine derivatives along with LPS.

The dendritic cells were subjected to pro-IL1b priming by the treatment with 500 ng/mL LPS for 3 hours, and then treated with benfotiamine at 0, 10, 50, or 100 and fursultiamine at 0, 10, 50, or 100 μM, for 15 minutes. Then, pro-IL1b was converted into IL-1β through pro-IL1b cleavage, followed by 5 mM ATP treatment for inducing inflammasome formation. After 30 minutes, IL-1β was assessed in supernatants, and the results are shown in FIG. 5 and Table 4.

TABLE 4

| | IL-1β (pg/mL) | | | | | |
|---|---|---|---|---|---|---|
| Benfotiamine | 0 μM[a,b] | 0 μM[b] | 0 μM | 10 μM | 50 μM | 100 μM |
| | 11.0950 | 37.0371 | 931.5479 | 912.2951 | 914.9398 | 914.2512 |

TABLE 4-continued

| | IL-1β (pg/mL) | | | | | |
|---|---|---|---|---|---|---|
| Fursultiamine | 0 μM[a,b] 11.0950 | 0 μM[b] 37.0371 | 0 μM 931.5479 | 10 μM 878.0075 | 50 μM 799.4891 | 100 μM 592.4987 |

([a]Dendritic cells are not stimulated by 100 ng/mL LPS, [b]No ATP treatment)

As can be seen from FIG. 5 and Table 4, benfotiamine could not inhibit the IL-1β expression increased by LPS, whereas fursultiamine significantly inhibited the IL-1β expression to levels of about 85.8237% and about 63.6037% at the concentrations of 50 μM and 100 μM, respectively.

3-3. Inhibition of CD40 and CD86 Expressions

Figure 6A:
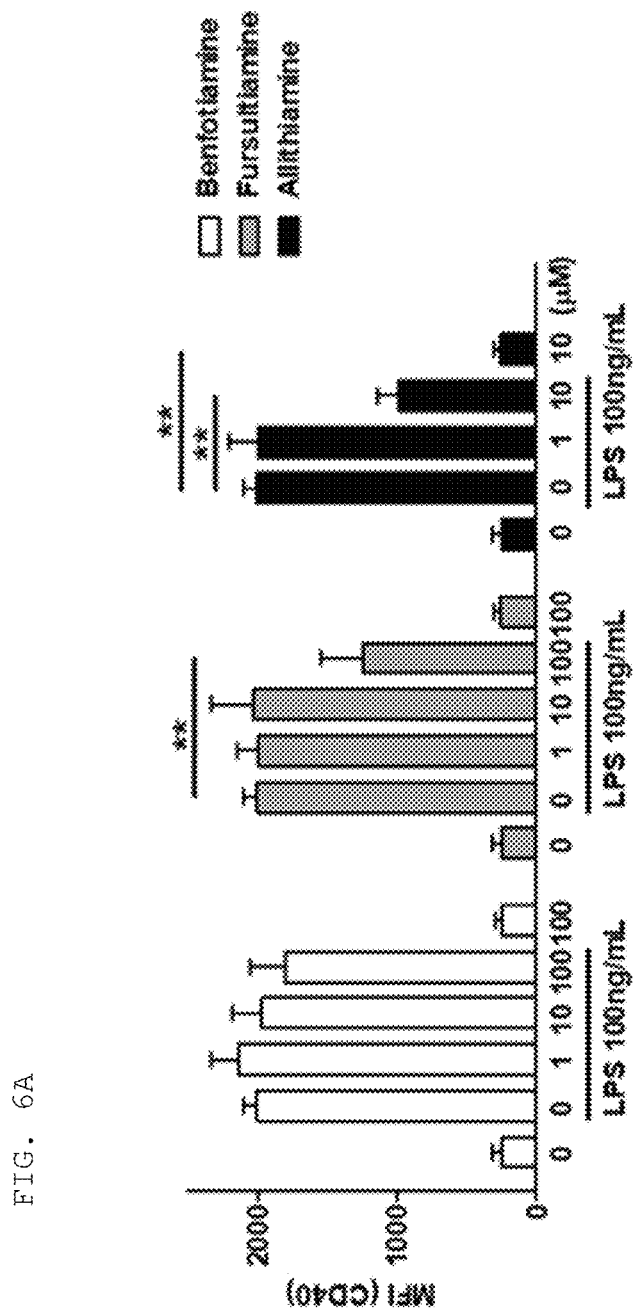
FIG. 6A shows graphs comparing CD40 expression levels in mice administered different concentrations of thiamine derivatives along with LPS.
Figure 6B:
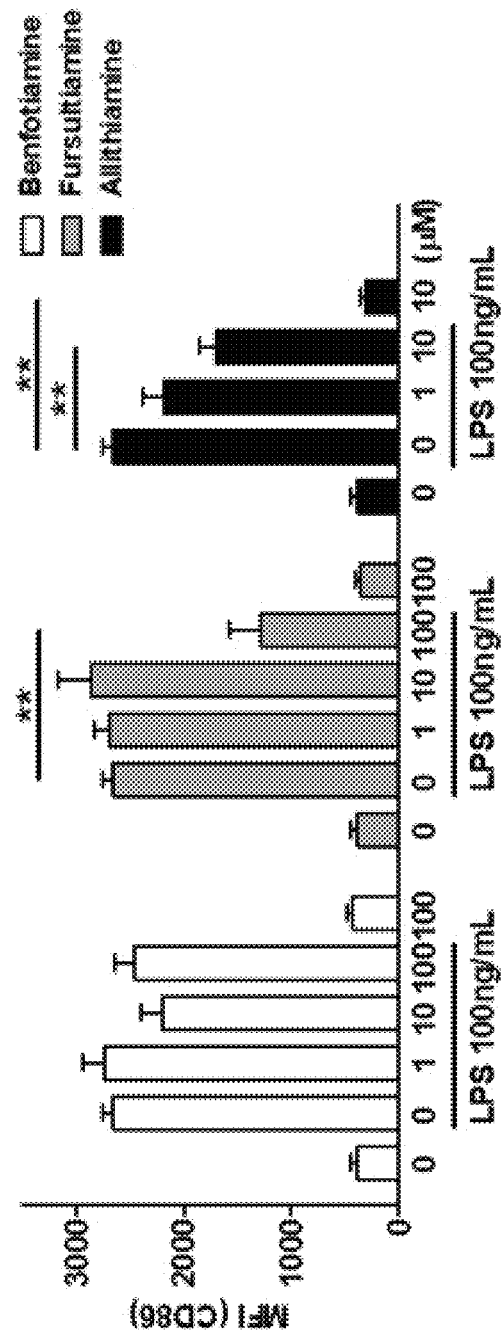
FIG. 6B shows graphs comparing CD86 expression levels in mice administered different concentrations of thiamine derivatives along with LPS.

The dendritic cells were measured for CD40 and CD86 in CD11c+ cells by flow cytometry, and the results are shown in FIGS. 6A and 6B and Tables 5 and 6.

TABLE 5

| | CD40 (Mean fluorescence intensity; MFI) | | | | | |
|---|---|---|---|---|---|---|
| Benfotiamine | 0 μM* 251 | 0 μM 2,004 | 1 μM 2,134 | 10 μM 1,975 | 100 μM 1,803 | 100 μM* 248 |

TABLE 5-continued

| | CD40 (Mean fluorescence intensity; MFI) | | | | | |
|---|---|---|---|---|---|---|
| Fursultiamine | 0 μM* 251 | 0 μM 2,004 | 1 μM 1,992 | 10 μM 2,026 | 100 μM 1,245 | 100 μM* 253 |
| Allithiamine | 0 μM* 251 | 0 μM 2,004 | 1 μM 1,998 | 10 μM 982 | 10 μM* 253 | — |

(*Dendritic cells are not stimulated by 100 ng/mL LPS.)

As can be seen from FIG. 6A and Table 5, benfotiamine could not inhibit the CD40 expression increased by LPS, whereas fursultiamine significantly inhibited the CD40 expression to a level of about 62% at the concentration of 100 μM and allithiamine significantly inhibited the CD40 expression to a level of about 49% at the concentration of 10 μM.

TABLE 6

| | CD86 (Mean fluorescence intensity; MFI) | | | | | |
|---|---|---|---|---|---|---|
| Benfotiamine | 0 μM* 382 | 0 μM 2,653 | 1 μM 2,734 | 10 μM 2,198 | 50 μM 2,448 | 100 μM 430 | 100 μM* 382 |
| Fursultiamine | 0 μM* 382 | 0 μM 2,653 | 1 μM 2,684 | 10 μM 2,864 | 50 μM 1,275 | 100 μM 351 | 100 μM* 382 |
| Allithiamine | 0 μM* 382 | 0 μM 2,653 | 1 μM 2,184 | 10 μM 1,704 | 10 μM* 304 | — | — |

(*Dendritic cells are not stimulated by 100 ng/mL LPS.)

As can be seen from FIG. 6B and Table 6, benfotiamine could not inhibit the CD86 expression increased by LPS, whereas fursultiamine significantly inhibited the CD86 expression to a level of about 13% at the concentration of 100 μM and allithiamine significantly inhibited the CD86 expression to a level of about 64% at the concentration of 10 μM.

3-4. Inhibition of TNFα Expression (In Vivo)

Figure 7B:
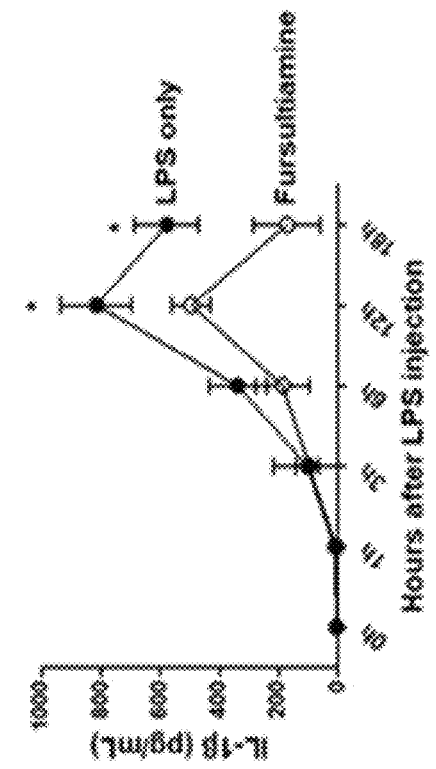
FIGS. 7A and 7B show graphs depicting the inhibition of TNFα or IL-1β expression by allithiamine and fursultiamine according to an experimental example of the present disclosure.
Figure 7A:
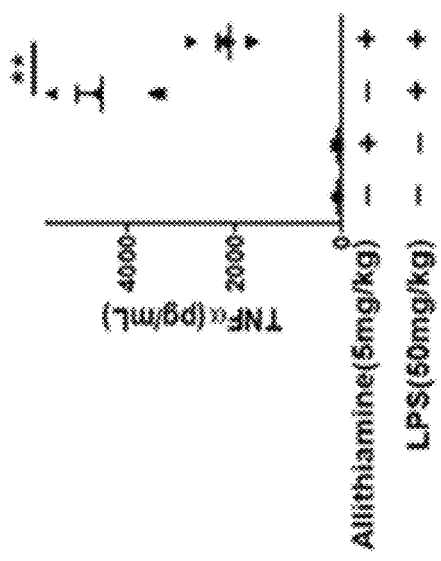

The inhibition of TNFα expression in vivo was investigated by the administration of 5 mg/kg allithiamine along with 50 mg/kg LPS, and the results are shown in FIG. 7A and Table 7.

TABLE 7

| Administration or not | LPS (50 mg/kg) | − | − | + | + |
|---|---|---|---|---|---|
| | Allithiamine (5 mg/kg) | − | + | − | + |
| | TNFα (pg/mL) | 79.561 | 82.442 | 4,484.206 | 2,084.883 |

As can be seen from FIG. 7A and Table 7, allithiamine reduced the TNFα expression, which had been increased to 4,484.206 pg/mL by LPS, to 2,084.883 pg/mL. Allithiamine significantly inhibited the TNFα expression considering a reduction of about 46.494%.

The inhibition of IL-1β expression was investigated by the administration of 100 mg/kg fursultiamine, instead of allithiamine, along with LPS, and the results are shown in FIG. 7B and Table 8.

TABLE 8

| | IL-1β (pg/mL) | | | | | |
|---|---|---|---|---|---|---|
| Hours | 0 h | 1 h | 3 h | 6 h | 12 h | 18 h |
| LPS only (50 mg/kg) | 5.147 | 11.290 | 103.144 | 338.739 | 815.804 | 577.802 |
| Fursultiamine (50 mg/kg) | 4.483 | 6.115 | 96.715 | 186.088 | 495.824 | 171.451 |

As can be seen from FIG. 7B and Table 8, the administration of fursultiamine reduced the IL-1β expression to a level of about 54.936%, from 338.739 pg/mL to 186.088 pg/mL, for 6 hours, relative the control without administration, in the mice with IL-1β expression increased by LPS. Especially, considering that fursultiamine, relative to the control, reduced the IL-1β expression to a level of about 60.777%, from 815.804 pg/mL to 495.824 pg/mL, for 12 hours, and to a level of about 29.673%, from 577.802 pg/mL to 171.451 pg/mL, for 18 hours, it was identified that fursultiamine significantly inhibited the IL-1β expression.

What is claimed is:

1. A method for alleviating or treating sepsis, the method comprising:
   administering to a subject a composition containing a thiamine derivative represented by chemical formula 1 or a pharmaceutically acceptable salt thereof:

[Chemical Formula 1]

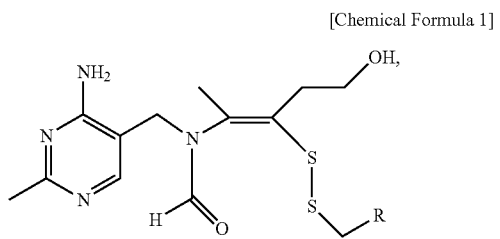

wherein R is selected from the group consisting of

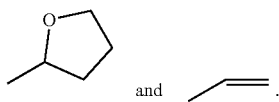

2. The method of claim 1, wherein the thiamine derivative is at least one selected from the group consisting of fursultiamine and allithiamine.

3. The method of claim 2, wherein the pharmaceutically effective amount of fursultiamine contained in the composition is 5-150 mg/kg according to the body weight of the subject to be administered.

4. The method of claim 2, wherein the pharmaceutically effective amount of allithiamine contained in the composition is 5-150 mg/kg according to the body weight of the subject to be administered.

5. The method of claim 1, wherein a causative pathogen of the sepsis is at least one selected from the group consisting of streptococci, staphylococci, *Escherichia coli*, pneumococcus, *Pseudomonas aeruginosa*, fungi, and *Klebsiella* modified *pseudomonas aeruginosa*.

* * * * *